(12) United States Patent
Zhou et al.

(10) Patent No.: US 6,403,840 B1
(45) Date of Patent: Jun. 11, 2002

(54) PROCESS FOR SYNTHESIZING OLEFIN OXIDES

(75) Inventors: Xiao Ping Zhou; Galen D. Stucky, both of Goleta, CA (US); Jeffrey H. Sherman, The Woodlands, TX (US)

(73) Assignee: GRT, Inc., Woodlands, TX (US)

( * ) Notice: Subject to any disclaimer, the term of this patent is extended or adjusted under 35 U.S.C. 154(b) by 0 days.

(21) Appl. No.: 09/951,581

(22) Filed: Sep. 11, 2001

Related U.S. Application Data

(63) Continuation-in-part of application No. 09/886,078, filed on Jun. 20, 2001.

(51) Int. Cl.$^7$ .............................................. C07C 41/00
(52) U.S. Cl. ...................................... 568/579
(58) Field of Search ......................................... 568/579

(56) References Cited

U.S. PATENT DOCUMENTS

| | | | |
|---|---|---|---|
| 3,172,915 A | 3/1965 | Borkowski et al. | 260/614 |
| 3,310,380 A | 3/1967 | Lester | 23/216 |
| 4,465,893 A | 8/1984 | Olah | 585/709 |
| 4,523,040 A | 6/1985 | Olah | 568/671 |
| 5,243,098 A | 9/1993 | Miller et al. | 568/893 |
| 5,334,777 A | 8/1994 | Miller et al. | 568/859 |
| 5,998,679 A | 12/1999 | Miller | 568/859 |

FOREIGN PATENT DOCUMENTS

| WO | PCT/IE99/05576 | 7/1999 |
|---|---|---|

OTHER PUBLICATIONS

Electrophilic Methane Conversion; by George A. Olah; Acc. Chem. Res. 1987, 20, 422–428, Loker Hydrocarbon Research Institute and Department of Chemistry, Univesity of Southern California, Los Angeles, California.

Antimony Pentafluoride/Graphite Catalyzed Oxidative Carbonylation of Methyl Halides with Carbon Monoxide and Copp Oxides (or Copper/Oxygen) to Methyl Acetate; by George A. Olah and Jozef Bukala; J. Org. Chem., 1990, 55, 4293–4297; Donald P. and Katherine B. Loker Hydrocarbon Research Institute and Department of Chemistry, University of Southern California, University Park, Los Angeles, California.

Superacid–Catalyzed Carbonylation of Methane, Methyl Halides, Methyl Alcohol, and Dimethyl Ether to Methyl Acetate a Acetic Acide; by Alessandro Bagno, Jozef Bukala, and George A. Olah; J. Org. Chem. 1990, 55, 4284–4289; Donald P. and Katherine B. Loker Hydrocarbon Research Institute, University of Southern California, University Park, Los Angeles, California.

Selective Monohalogenation of Methane over Supported Acid or Platinum Metal Catalysts and Hydrolysis of Methyl Halides over y–Alumina–Supported Metal Oxide/Hydroxide Catalysts. A Feasible Path for the Oxidative Conversion of Methane into Methyl Alcohol/Dimethyl Ether; George B. Olah, et al.; Contribution from the Donald P. and Katherine B. Loker Hydrocarbon Research Institute and Department of Chemistry, University of Southern California, Los Angeles, CA; received Apr. 22, 1985.

*Primary Examiner*—Samuel Barts
*Assistant Examiner*—Elvis O. Price
(74) *Attorney, Agent, or Firm*—Michael A. O'Neil

(57) ABSTRACT

Olefin bromohydrins and/or alkane dibromides are reacted with metal oxide to form olefin oxides. The metal bromide is converted to form the original metal oxide and bromine, both of which are recycled.

55 Claims, No Drawings

PROCESS FOR SYNTHESIZING OLEFIN OXIDES

CROSS REFERENCE TO RELATED APPLICATION

This is a continuation-in-part application under 37 C.F.R. §1.63 of application Ser. No. 09/886,078 filed Jun. 20, 2001, currently pending.

TECHNICAL FIELD

This invention relates generally to the synthesis of olefin oxides, and more particularly to an economical and safe process for synthesizing propylene oxide and other olefin oxides.

BACKGROUND AND SUMMARY OF THE INVENTION

Co-pending application Ser. No. 09/886,078 filed Jun. 20, 2001 and assigned to the assignee hereof is incorporated herein by reference. The co-pending application discloses and claims a process for synthesizing alcohols and ethers from alkanes. The process involves reacting an alkane with bromine to form the corresponding alkyl bromide and hydrogen bromide. The alkyl bromide and the hydrogen bromide are reacted with a metal oxide to produce the corresponding alcohol and/or ether, and metal bromide. The metal bromide is oxidized to form the original metal oxide and bromine, both of which are recycled.

The present invention employs a similar procedure to synthesize olefin oxides, particularly propylene oxide. Propylene oxide has heretofore been produced using a wide variety of procedures, none of which is particularly satisfactory.

The oldest and most widely used procedure for preparing propylene oxide is the propylene chlorohydrin process. An early propylene chlorohydrin technique involved electrolyzation of propylene in aqueous potassium chloride to prepare propylene chlorohydrin which was then dehydrohalogenated to produce propylene oxide. At the present time propylene oxide is prepared by reacting propylene with chlorine/water to prepare propylene chlorohydrin, then reacting the propylene chlorohydrin with aqueous calcium hydroxide, sodium hydroxide or calcium carbonate to obtain propylene oxide. A major drawback to the propylene chlorohydrin process involves the fact that the manufacture of a given quantity of propylene oxide necessarily results in the manufacture of a like or greater quantity of various salts which have little commercial value. A further disadvantage of the propylene chlorohydrin process is the fact that the propylene oxide product must be separated from large quantities of water, generally through steam stripping.

Propylene oxide can also be manufactured utilizing the ethylbenzene process. As currently practiced the ethylbenzene process involves reacting ethylbenzene with oxygen to generate ethylbenzene hydroperoxide which is then reacted with propylene to obtain propylene oxide and alpha phenylethanol. The alpha phenylethanol is then converted to styrene by dehydration. The major drawbacks to the ethylbenzene process involves the production of styrene in equal quantities with the desired propylene oxide and the use of ethylbenzene hydroperoxide, which is both explosive and subject to decomposition.

Cumene can also be used to manufacture propylene oxide. The cumene is oxidized to produce cumene hydroperoxide which is then reacted with propylene to form propylene oxide and cumyl alcohol. The cumyl alcohol is reduced to cumene by reaction with hydrogen over a catalyst and is recycled. The drawbacks to the cumene process include the use of large amounts of cumene hydroperoxide which is highly explosive and the consumption of expensive hydrogen.

A fourth process for manufacturing propylene oxide is known as the tert-butane hydroperoxide process. In accordance therewith isobutane is oxidized by reaction with oxygen to obtain tertiary butane hydroperoxide, which is then reacted with propylene to form propylene oxide and tert-BuOH. The drawbacks to the process include the direct reaction of butane with oxygen, the use of dangerous tert-butane hydroperoxide, and the production of tert-BuOH as a byproduct.

Still another process for producing propylene oxide is known as the hydrogen peroxide process. In accordance therewith, propylene is reacted with hydrogen peroxide in a solvent such as methanol over a catalyst. Drawbacks to the process include the fact that the reaction rate is very slow and the fact that expensive hydrogen is necessarily consumed to form hydrogen peroxide.

A sixth method of synthesizing propylene oxide involves direct oxidation of propylene. In accordance with the procedure, propylene is reacted with oxygen over a catalyst to generate propylene oxide. As will be apparent, safety considerations dictate that the process is very carefully controlled. Other drawbacks include low conversion rates, typically below 10% and low selectivity, typically below 40%.

The present invention comprises a method of synthesizing propylene oxide and other olefin oxides which overcomes the foregoing and other difficulties that have long since characterized the prior art. In accordance with the broader aspects of the invention, an olefin bromohydrin or an alkane dibromide is reacted with a metal oxide to form olefin oxide and metal bromide. The metal bromide is converted to obtain the original metal oxide and bromine, both of which are recycled.

DETAILED DESCRIPTION

In the process of the present invention an olefin bromohydrin and/or an alkane dibromide (such as propylene bromohydrin and/or 1,2-dibromopropane) is reacted with a metal oxide to synthesize olefin oxide (such as propylene oxide), with the corresponding metal bromide being formed as a by product. The metal bromide is converted back to the original metal oxide and bromine, both of which are recycled. The process consumes nothing other than olefin and oxygen. There is no direct contact between oxygen and olefin, and the process does not result in large amounts of HCl or $Cl_2$ in water as in the traditional olefin chlorohydrin process. A further benefit of the process results from the easy separation of olefin oxide from the alkane dibromide rather than the separation of the olefin oxide from aqueous alkaline waste.

EXAMPLE

Zr Solution Preparation $Zr(OCH_2CH_2CH_3)_4$ (70(w) % in isopropanol, 112.6 ml) was dissolved into acetic acid (275 ml) under stirring. After stirring for 10 minutes, the solution was diluted by water to make a total volume of 500 ml. A solution with a Zr concentration of 0.5M was obtained.

Preparation of Metal Oxide M

M1

Cu(NO$_3$)$_2$ (0.5M, 64.0 ml) solution was added into Zr solution (0.5M, 64.0 ml) (as prepared above). After stirring for a few seconds, a gel was obtained. The gel was dried at 110° C. for 4 hours, then heated to 500° C. within 6 hours, and calcined at 500° C. for 4 hours. CuO/ZrO$_2$ metal oxide (M1) was obtained.

M2

Cu(NO$_3$)$_2$ (0.5M, 6.8 ml) solution was mixed with BaBr$_2$ (0.5M, 1.2 ml). A clear solution was obtained. The solution was added into Zr solution (0.5M, 8.0 ml) (as prepared above). After stirring for a few seconds, a gel was obtained. The gel was dried at 110° C. for 4 hours, then heated to 500° C. within 6 hours, and calcined at 500° C. for 4 hours. BaBr$_2$CuO/ZrO$_2$ metal oxide (M2) was obtained.

M3

Cu(NO$_3$)$_2$ (0.5M, 7.6 ml) solution was mixed with CaBr$_2$ (0.5M, 0.4 ml). A clear solution was obtained. The solution was added into Zr solution (0.5M, 8.0 ml) (as prepared above). After stirring for a few seconds, a gel was obtained. The gel was dried at 110° C. for 4 hours, then heated to 500° C. within 6 hours, and calcined at 500° C. for 4 hours. CaBr$_2$CuO/ZrO$_2$ metal oxide (M3) was obtained.

M4

Cu(NO$_3$)$_2$ (0.5M, 7.6 ml) solution was mixed with SrBr$_2$ (0.5M, 0.4 ml). A clear solution was obtained. The solution was added into Zr solution (0.5M, 8.0 ml) (as prepared above). After stirring for a few seconds, a gel was obtained. The gel was dried at 110° C. for 4 hours, then heated to 500° C. within 6 hours, and calcined at 500° C. for 4 hours. SrBr$_2$CuO/ZrO$_2$ metal oxide (M4) was obtained.

Testing

Reaction on M1

Propylene bromohydrin (1.00 ml/hour) and helium (2.0 ml/minute) were passed through a reactor that was packed with 3.0000 gram M1, which was heated to 100° C. Within the first 2 hours, an average propylene bromohydrin conversion of 35%, with 50% propylene oxide average selectivity and 50% acetone selectivity was obtained. In the second hour, only propylene oxide was obtained.

1,2-dibromopropane 1,2-dibromopropane (1.00 ml/hour) and helium (2.0 ml/minute) were passed through a reactor packed with M at 100° C. Within the first 2 hours, an average 1,2-dibromopropane conversion of 40%, with 30% propylene oxide average selectivity and 70% acetone selectivity was obtained.

Reaction on M2

Propylene bromohydrin (1.00 ml/hour) and helium (2.0 ml/minute) were passed through a reactor that was packed with 1.1784 gram M2, which was heated to 100° C. Within the first 2 hours, an average propylene bromohydrin conversion of 50%, with 67% propylene oxide average selectivity and 33% acetone selectivity was obtained.

When running M2 at 80° C., 40% propylene bromohydrin conversion with 75% propylene oxide selectivity was obtained.

1,2-dibromopropane 1,2-dibromopropane (1.00 ml/hour) and helium (2.0 ml/minute) were passed through a reactor packed with M2 at 100° C. Within the first 2 hours, an average 1,2-dibromopropane conversion of 42%, with 62% propylene oxide average selectivity was obtained.

Reaction on M3

Propylene bromohydrin (0.50 ml/hour) and nitrogen (5.0 ml/minute) were passed through a reactor that packed with 0.8286 gram M3, which was heated to 120° C. Within the first 1.5 hours, an average propylene bromohydrin conversion of 50%, with 41% propylene oxide average selectivity was obtained.

1,2-dibromopropane 1,2-dibromopropane (1.00 ml/hour) (0.50 ml/hour) and nitrogen (5.0 ml/minute) were passed through a reactor that packed with 0.8286 gram M3, which was heated to 100° C. Within the first 1.5 hours, an average propylene bromohydrin conversion of 40%, with 59% propylene oxide average selectivity was obtained.

Reaction on M4

Propylene bromohydrin (0.50 ml/hour) and nitrogen (5.0 ml/minute) were passed through a reactor that packed with 0.8836 gram M4, which was heated to 120° C. Within the first 2 hours, an average propylene bromohydrin conversion of 40%, with 56% propylene oxide average selectivity was obtained.

In the above reactions, the metal oxide can be an oxide of the following metals: Ti, Zr, Hf, V, Nb, Ta, Cr, Mo, W, Mn, Re, Fe, Ru, Co, Rh, Ir, Ni, Pd, Pt, Cu, Ag, Au, Zn, Cd, Al, Ga, In, Tl, Ge, Sn, Pb, P, Sb, Bi, Sc, Y, Mg, Ca, Sr, Ba, Na, Li, K, La, Ce, Pr, Nd, Sm, Eu, Gd, Tb, Er, Yb, Lu, and Cs, or mixtures thereof.

The reactions can be carried out at a temperature range of between about 50° C. to about 600° C. The reactions pressure can be from about 1 to about 200 atm. The reaction can be carried out with or without helium. The metal bromide resulting from the process can be converted in oxygen or in air to obtain the original metal oxide and bromine, both of which are recycled. The conversion reaction takes place at a temperature range of between about 50 to about 700° C. and a pressure range from about 1 to 300 atm.

The method of the present invention operates on a continuous or batch basis to convert olefin bromohydrins and/or alkane dibromides to olefins oxides. The method of the present invention operates at relatively low temperatures and at low pressures and is therefore economical in use. The favorable economics of the method also result from the fact that only the bromohydrin and/or dibromide reactants and oxygen are consumed. The method does not involve direct contact between the reactants and oxygen and is therefore relatively safe.

Although preferred embodiments of the invention have been illustrated in the accompanying Drawings and described in the foregoing Detailed Description, it will be understood that the invention is not limited to the embodiments disclosed but is capable of numerous rearrangements, modifications, and substitutions of parts and elements without departing from the spirit of the invention.

What is claimed is:

1. A method for synthesizing olefin oxides comprising:
   providing a quantity of a reactant selected from the group including bromohydrins and alkane dibromides;
   reacting the selected reactant with a metal oxide and thereby forming olefin oxide and a metal bromide;
   converting the metal bromide to form the original metal oxide and bromine;
   recycling the metal oxide; and
   recycling the bromine.

2. The method according to claim 1 wherein the reacting step is carried out at a pressure of between about 1 and about 300 ATM.

3. The method according to claim 1 wherein the reacting step is carried out at a temperature of between about 50° C. and about 600° C.

4. The process according to claim 1 wherein the reacting step is carried out continuously.

5. The process according to claim 1 wherein the reacting step is carried out in a batch reaction.

6. The method according to claim 1 wherein the step of converting the metal bromide to form the original metal oxide and bromine, the step of recycling the metal oxide, and the step of recycling the bromine are carried out continuously.

7. The method according to claim 1 wherein the step of converting the metal bromide to form the original metal oxide and bromine, the step of recycling the metal oxide, and the step of recycling the bromine are carried out in a batch reaction.

8. A method for converting an olefin to is corresponding olefin oxide comprising:

providing a quantity of an olefin;

providing a quantity of bromine;

providing a quantity of water reacting the olefin with bromine/$H_2O$ and thereby forming the corresponding olefin bromohydrin;

reacting the olefin bromohydrin with a metal oxide and thereby forming the corresponding olefin oxide;

converting the metal bromide to form the original metal oxide and bromine;

recycling the metal oxide; and recycling the bromine.

9. The method according to claim 8 wherein the step of reacting the olefin bromohydrin with the metal oxide is carried out a pressure of between about 1 to about 300 ATM.

10. The method according to claim 8 wherein the step reacting the olefin bromohydrin with the metal oxide is carried out at a temperature of between about 50° C. and about 600° C.

11. The method according to claim 8 wherein the metal oxide includes an oxide of at least one of the following metals:

Ti, Zr, Hf, V, Nb, Ta, Cr, Mo, W, Mn, Re, Fe, Ru, Co, Rh, Ir, Ni, Pd, Pt, Cu, Ag, Au, Zn, Cd, Al, Ga, In, Tl, Ge, Sn, Pb, P, Sb, Bi, Sc, Y, Mg, Ca, Sr, Ba, Na, Li, K, La, Ce, Pr, Nd, Sm, Eu, Gd, Tb, Er, Yb, Lu, and Cs.

12. The process according to claim 8 wherein the step of reacting the olefin bromohydrin with the metal oxide is carried out continuously.

13. The process according to claim 8 wherein the step of reacting the olefin bromohydrin with the metal oxide is carried out in a batch reaction.

14. The method according to claim 8 wherein the step of converting the metal bromide to form the original metal oxide and bromine, the step of recycling the metal oxide, and the step of recycling the bromine are carried out continuously.

15. The method according to claim 8 wherein the step of converting the metal bromide to form the original metal oxide and bromine, the step of recycling the metal oxide, and the step of recycling the bromine are carried out in a batch reaction.

16. A method for converting an olefin to its corresponding olefin oxide comprising:

providing a quantity of an olefin;

providing a quantity of bromine;

reacting the olefin with the bromine and thereby forming the corresponding alkane dibromide;

reacting the alkane dibromide with a metal oxide and thereby forming the corresponding olefin oxide;

converting the metal bromide to form the original metal oxide and bromine;

recycling the metal oxide; and recycling the bromine.

17. The method according to claim 16 wherein the step of reacting the alkane dibromide with the metal oxide is carried out at a pressure of between about 1 to about 300 ATM.

18. The method according to claim 16 wherein the step of reacting the alkane dibromide with the metal oxide is carried out at a temperature of between about 50° C. and about 600° C.

19. The process according to claim 16 wherein the step of reacting the alkane dibromide with the metal oxide is carried out continuously.

20. The process according to claim 16 wherein the step of reacting the alkane dibromide with the metal oxide is carried out in a batch reaction.

21. The method according to claim 16 wherein the step of converting the metal bromide to form the original metal oxide and bromine, the step of recycling the metal oxide, and the step of recycling the bromine are carried out continuously.

22. The method according to claim 16 wherein the step of converting the metal bromide to form the original metal oxide and bromine, the step of recycling the metal oxide, and the step of recycling the bromine are carried out in a batch reaction.

23. The method according to claim 16 wherein the metal oxide includes an oxide of at least one of the following metals:

Ti, Zr, Hf, V, Nb, Ta, Cr, Mo, W, Mn, Re, Fe, Ru, Co, Rh, Ir, Ni, Pd, Pt, Cu, Ag, Au, Zn, Cd, Al, Ga, In, Tl, Ge, Sn, Pb, P, Sb, Bi, Sc, Y, Mg, Ca, Sr, Ba, Na, Li, K, La, Ce, Pr, Nd, Sm, Eu, Gd, Tb, Er, Yb, Lu, and Cs.

24. A method for synthesizing olefin oxides from alkanes comprising:

providing a quantity of an alkane selected from the group including ethane, propane, butane, isobutane, pentanes, cyclohexane and hexanes;

providing a quantity of bromine;

reacting the selected alkane and the bromine and thereby forming the corresponding alkane dibromide;

reacting the alkane dibromide with a metal oxide and thereby forming olefin oxide and a metal bromide;

recovering the thus formed olefin oxide;

converting the metal bromide to form the original metal oxide and bromine;

recycling the metal oxide; and recycling the bromine.

25. The method according to claim 24 wherein the step of reacting the alkane dibromide with the metal oxide is carried out at a pressure of between about 1 and about 300 ATM.

26. The method according to claim 24 wherein the step of reacting the alkane dibromide with the metal oxide is carried out at a temperature of between about 50° C. and about 600° C.

27. The process according to claim 24 wherein the steps of forming the alkane dibromide and reacting the alkane dibromide with a metal oxide are carried out continuously.

28. The process according to claim 24 wherein the steps forming the alkane dibromide and the step of reacting the alkane dibromide with a metal oxide are carried out in a batch reaction.

29. The method according to claim 24 wherein the step of converting the metal bromide to form the original metal oxide and bromine, the step of recycling the metal oxide, and the step of recycling the bromine are carried out continuously.

30. The method according to claim 24 wherein the step of oxidizing the metal bromide to form the original metal oxide and bromine, the step of recycling the metal oxide, and the step of recycling the bromine are carried out in batch reactions.

31. The method according to claim 24 wherein the metal oxide includes an oxide of at least one of the following metals:

Ti, Zr, Hf, V, Nb, Ta, Cr, Mo, W, Mn, Re, Fe, Ru, Co, Rh, Ir, Ni, Pd, Pt, Cu, Ag, Au, Zn, Cd, Al, Ga, In, Tl, Ge, Sn, Pb, P, Sb, Bi, Sc, Y, Mg, Ca, Sr, Ba, Na, Li, K, La, Ce, Pr, Nd, Sm, Eu, Gd, Tb, Er, Yb, Lu, and Cs.

32. The method according to claim 24 further characterized by forming 1,2 dibromopropane over a brominating catalyst.

33. The method according to claim 32 wherein the step of forming 1,2 dibromopropane is practiced using heat.

34. The method according to claim 32 wherein the step of forming 1,2 dibromopropane is practiced using electromagnetic radiation.

35. The method according to claim 32 wherein the step of forming 1,2 dibromopropane is practiced using a combination of a brominating catalyst, heat and electromagnetic radiation.

36. A method for synthesizing olefin oxides from olefins comprising:

providing a quantity of an olefin selected from the group including ethylene, propylene butylene, pentenes, cyclohexene and hexenes;

providing a quantity of bromine;

providing a quantity of water reacting the selected olefin and bromine/$H_2O$ and thereby forming the corresponding olefin bromohydrin;

reacting the olefin bromohydrin with a metal oxide and thereby forming olefin oxide and a metal bromide;

recovering the thus formed olefin oxide;

converting the metal bromide to form the original metal oxide and bromine;

recycling the metal oxide catalyst; and recycling the bromine.

37. The method according to claim 36 wherein the step of reacting the bromohydrin with the metal oxide is carried out at a pressure of between about 1 and about 300 ATM.

38. The method according to claim 36 wherein the step of reacting the bromohydrin with the metal oxide is carried out at a temperature of between about 50° C. and about 600° C.

39. The process according to claim 36 wherein the steps of forming the bromohydrin and reacting the bromohydrin with a metal oxide are carried out continuously.

40. The process according to claim 36 wherein the step forming the bromohydrin and the step of reacting the bromohydrin with a metal oxide are carried out in a batch reaction.

41. The method according to claim 36 wherein the step of converting the metal bromide to form the original metal oxide and bromine, the step of recycling the metal oxide, and the step of recycling the bromine are carried out continuously.

42. The method according to claim 36 wherein the step of converting the metal bromide to form the original metal oxide and bromine, the step of recycling the metal oxide, and the step of recycling the bromine are carried out in batch reactions.

43. The method according to claim 36 wherein the metal oxide includes an oxide of at least one of the following metals:

Ti, Zr, Hf, V, Nb, Ta, Cr, Mo, W, Mn, Re, Fe, Ru, Co, Rh, Ir, Ni, Pd, Pt, Cu, Ag, Au, Zn, Cd, Al, Ga, In, Tl, Ge, Sn, Pb, P, Sb, Bi, Sc, Y, Mg, Ca, Sr, Ba, Na, Li, K, La, Ce, Pr, Nd, Sm, Eu, Gd, Tb, Er, Yb, Lu, and Cs.

44. A method for synthesizing propylene oxide from propane comprising:

providing a quantity of propane;

providing a quantity of bromine;

reacting the propane and the bromine and thereby forming 1,2-dibromopropane;

reacting the 1,2-dibromopropane with a metal oxide and thereby forming propylene oxide and a metal bromide;

recovering the thus formed propylene oxide;

converting the metal bromide to form the original metal oxide and bromine;

recycling the metal oxide catalyst; and recycling the bromine.

45. The method according to claim 44 wherein the step of reacting the 1,2-dibromopropane with the metal oxide is carried out at a pressure of between about 1 and about 300 ATM.

46. The method according to claim 41 wherein the step of reacting the 1,2-dibromopropane with the metal oxide is carried out at a temperature of between about 50° C. and about 600° C.

47. The process according to claim 44 wherein the step of forming the 1,2-dibromopropane and the step of reacting the 1,2-dibromopropane with a metal oxide are carried out continuously.

48. The process according to claim 44 wherein the step forming the 1,2-dibromopropane and the step of reacting the 1,2-dibromopropane with a metal oxide are carried out in a batch reaction.

49. The method according to claim 44 wherein the step of converting the metal bromide to form the original metal oxide catalyst and bromine, the step of recycling the metal oxide catalyst, and the step of recycling the bromine are carried out continuously.

50. The method according to claim 44 wherein the step of converting the metal bromide to form the original metal oxide catalyst and bromine, the step of recycling the metal oxide, and the step of recycling the bromine are carried out in batch reactions.

51. The method according to claim 44 wherein the metal oxide(s) is the oxide or oxide mixtures of the following metals:

Ti, Zr, Hf, V, Nb, Ta, Cr, Mo, W, Mn, Re, Fe, Ru, Co, Rh, Ir, Ni, Pd, Pt, Cu, Ag, Au, Zn, Cd, Al, Ga, In, Tl, Ge, Sn, Pb, P, Sb, Bi, Sc, Y, Mg, Ca, Sr, Ba, Na, Li, K, La, Ce, Pr, Nd, Sm, Eu, Gd, Tb, Er, Yb, Lu, and Cs.

52. The method according to claim 44 wherein the step of forming 1,2 dibromopropane is practiced over a brominating catalyst.

53. The method according to claim 44 wherein the step of forming 1,2 dibromopropane is practiced using heat.

54. The method according to claim 44 wherein the step of forming 1,2 dibromopropane is practiced using electromagnetic radiation.

55. The method according to claim 44 wherein the step of forming 1,2 dibromopropane is practiced using a combination of a brominating catalyst, heat and electromagnetic radiation.

* * * * *

UNITED STATES PATENT AND TRADEMARK OFFICE
CERTIFICATE OF CORRECTION

PATENT NO. : 6,403,840 B1
DATED : June 11, 2002
INVENTOR(S) : Jeffrey H. Sherman et al.

It is certified that error appears in the above-identified patent and that said Letters Patent is hereby corrected as shown below:

Column 5,
Line 15, replace "to is corresponding" with -- to its corresponding --.
Line 19, replace "quantity of water" with -- quantity of water; --
Line 30, replace "carried out a pressure" with -- carried out at a pressure --.

Column 7,
Lines 12, 15, 17 and 20, replace "1,2 dibromopropane" with -- 1,2-dibromopropane --.
Line 29, replace "quantity of water" with -- quantity of water; --.

Column 8,
Lines 52, 55, 57 and 60, replace "1,2 dibromopropane" with -- 1,2-dibromopropane --.

Signed and Sealed this

Fifth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,403,840 B1
DATED : June 11, 2002
INVENTOR(S) : Ziao Ping Zhou, Galen D. Stuck and Jeffrey H. Sherman It is certified that error appears in the above-identified patent and that said Letters Patent is hereby corrected as shown below:

<u>Title page,</u>
Item [73], Assignee, please add -- The Regents of the University of California, Oakland, CA (US) --

Signed and Sealed this

Twenty-seventh Day of April, 2004

JON W. DUDAS
*Acting Director of the United States Patent and Trademark Office*